US 8,000,776 B2

(12) United States Patent
Gono

(10) Patent No.: US 8,000,776 B2
(45) Date of Patent: Aug. 16, 2011

(54) IMAGING APPARATUS

(75) Inventor: Kazuhiro Gono, Sagamihara (JP)

(73) Assignee: Olympus Corporation, Tokyo (JP)

( * ) Notice: Subject to any disclaimer, the term of this patent is extended or adjusted under 35 U.S.C. 154(b) by 1381 days.

(21) Appl. No.: 10/534,921

(22) PCT Filed: Nov. 18, 2003

(86) PCT No.: PCT/JP03/14641
§ 371 (c)(1),
(2), (4) Date: May 9, 2005

(87) PCT Pub. No.: WO2004/052187
PCT Pub. Date: Jun. 24, 2004

(65) Prior Publication Data
US 2006/0241349 A1      Oct. 26, 2006

(30) Foreign Application Priority Data

Dec. 12, 2002   (JP) .................................. 2002-361325
Sep. 5, 2003    (JP) .................................. 2003-314206

(51) Int. Cl.
*A61B 6/00*         (2006.01)
(52) U.S. Cl. ......... 600/476; 600/109; 600/160; 600/178
(58) Field of Classification Search .......... 600/407–410, 600/424, 476–480
See application file for complete search history.

(56) References Cited

U.S. PATENT DOCUMENTS

| 5,699,798 | A | * | 12/1997 | Hochman et al. ............. 600/420 |
| 6,081,612 | A | * | 6/2000 | Gutkowicz-Krusin et al. .............................. 382/128 |
| 6,091,984 | A | * | 7/2000 | Perelman et al. ............ 600/476 |
| 6,161,031 | A | * | 12/2000 | Hochman et al. ............. 600/407 |
| 6,208,886 | B1 | * | 3/2001 | Alfano et al. ................ 600/473 |
| 6,241,672 | B1 | * | 6/2001 | Hochman et al. ............. 600/431 |
| 6,293,911 | B1 | * | 9/2001 | Imaizumi et al. ............ 600/160 |
| 6,529,768 | B1 | * | 3/2003 | Hakamata ..................... 600/476 |
| 6,602,186 | B1 | * | 8/2003 | Sugimoto et al. ............ 600/126 |
| 6,639,674 | B2 | * | 10/2003 | Sokolov et al. .............. 356/369 |

(Continued)

FOREIGN PATENT DOCUMENTS

JP          2000-014629        1/2000

(Continued)

OTHER PUBLICATIONS

Backman, V., et al. "Measuring Cellular Structure at Submicrometer Scale with Light Scattering Spectroscopy", IEEE Journal on Selected Topics in Quantum Electronics, vol. 7, No. 6, Nov./Dec. 2001, pp. 887-893.
Gurjar, R., et al. "Imaging human epithelial properties with polarized light-scattering spectroscopy", Nature Medicine, vol. 7, No. 11, Nov. 2001, pp. 1245-1248.
Narihiro, Matoba et al., "Multispectral Image Capturing System", ITE Technical Report (2000), vol. 24, No. 3, pp. 25-30.

(Continued)

*Primary Examiner* — Sanjay Cattungal
(74) *Attorney, Agent, or Firm* — Scully, Scott, Murphy & Presser, P.C.

(57) ABSTRACT

An image processing circuit includes a spectrum estimating portion for inputting image data, obtaining data required for spectrum estimation from an estimation data supplying portion and estimating spectrums of pixels, a scattering feature calculating portion for calculating several scattering features based on spectrums of pixels from the spectrum estimating portion and data required for feature calculation from the feature calculation data supplying portion, and a color image generating portion for performing a display color calculation based on a scattering feature image from the scattering feature calculating portion and for determining RGB values of respective pixels and outputting RGB images in order to display scattering features as a color image.

2 Claims, 16 Drawing Sheets

U.S. PATENT DOCUMENTS

| | | | |
|---|---|---|---|
| 6,697,652 B2* | 2/2004 | Georgakoudi et al. | 600/310 |
| 6,772,003 B2* | 8/2004 | Kaneko et al. | 600/476 |
| 6,912,412 B2* | 6/2005 | Georgakoudi et al. | 600/310 |
| 6,922,583 B1* | 7/2005 | Perelman et al. | 600/476 |
| 7,054,002 B1* | 5/2006 | Sevick-Muraca et al. | 356/317 |
| 7,179,222 B2* | 2/2007 | Imaizumi et al. | 600/109 |
| 7,333,189 B2* | 2/2008 | Fulghum et al. | 356/73 |
| 7,404,929 B2* | 7/2008 | Fulghum, Jr. | 422/82.05 |
| 2002/0135752 A1* | 9/2002 | Sokolov et al. | 356/39 |
| 2002/0143243 A1* | 10/2002 | Georgakoudi et al. | 600/310 |
| 2003/0013973 A1* | 1/2003 | Georgakoudi et al. | 600/473 |
| 2003/0060678 A1* | 3/2003 | Watai et al. | 600/109 |
| 2003/0139650 A1* | 7/2003 | Homma | 600/181 |
| 2003/0191368 A1* | 10/2003 | Wang et al. | 600/160 |
| 2003/0229270 A1* | 12/2003 | Suzuki et al. | 600/178 |
| 2003/0231309 A1* | 12/2003 | Fulghum et al. | 356/338 |
| 2003/0232445 A1* | 12/2003 | Fulghum, Jr. | 436/63 |
| 2004/0072356 A1* | 4/2004 | Senisterra et al. | 436/63 |

FOREIGN PATENT DOCUMENTS

| | | |
|---|---|---|
| JP | 2002-034893 | 2/2002 |
| JP | 2002-034908 | 2/2002 |
| JP | 2002-095635 | 4/2002 |
| JP | 2003-047588 | 2/2003 |
| JP | 2003-527916 | 9/2003 |
| WO | WO 99/18845 | 4/1999 |
| WO | WO 01/72216 A2 | 10/2001 |

OTHER PUBLICATIONS

Backman, Vadim, et al., "Polarized Light Scattering Spectroscopy for Quantitative Measurement of Epithelial Cellular Structures In Situ", IEEE Journal of Selected Topics in (Quantum Electronics (1999), vol. 5, No. 4, pp. 1019-1026.

* cited by examiner

NARROW-BAND MULTIBAND FILTER

DISTRIBUTION OF PARTICLE SIZE

FLOW OF MODEL CALCULATION

CALCULATION OF SCATTERING FEATURE

FIRST LAYER

SECOND LAYER

IMAGE OF
FIRST LAYER

IMAGE OF
SECOND LAYER

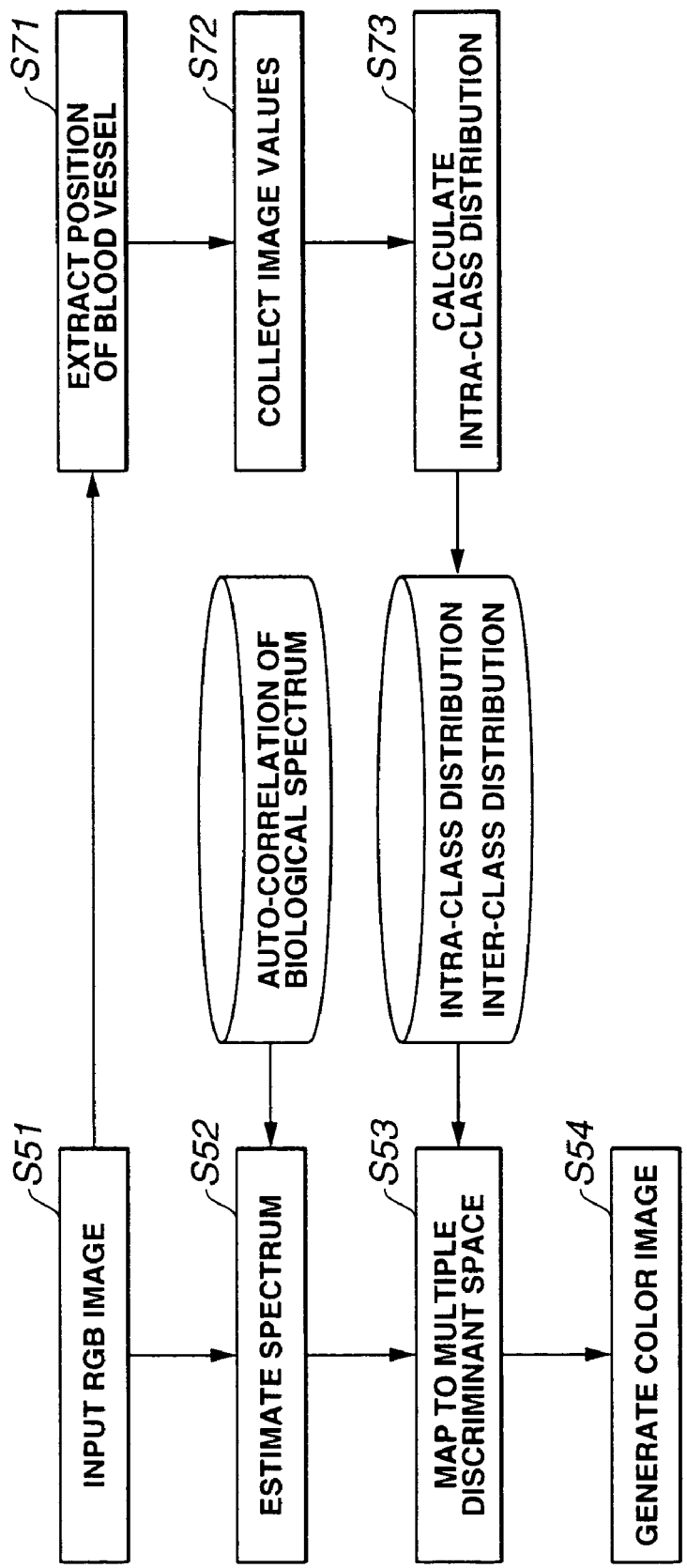

IMAGING APPARATUS

TECHNICAL FIELD

The present invention relates to an imaging apparatus for performing scattering imaging processing of a living body tissue.

BACKGROUND ART

It is known that many digestive tract tumor diseases such as an esophagus cancer are formed from a basal layer within epitheliums, which is the most outer layer of a mucous membrane of a digestive tract. As the malignant degree increases, abnormal cells formed from the basal layer increase and, at last, the entire of epitheliums is replaced. The tumor change in the epitheliums involves a cell simple variant and pathological changes in structure, that is so-called a structural variant. As a result, an irregular tissue arrangement is exhibited which is different from a normal pathological image.

An object of an endoscopic diagnosis is to find this kind of tumor as early as possible. Finding this kind of tumor at an earlier stage may increase the possibility for curing the tumor completely increases by performing a less invasive operation such as an endoscopic treatment.

However, some kinds of tumor such as an esophagus cancer do not have clear form (that is, a polyp or subsidence form) very much at an earlier stage and cannot be always found easily.

Many propositions have been made so far for finding and discriminating tumors having poor changes in form at an earlier stage.

Scattering spectroscopy and scattering imaging (as disclosed in Japanese Unexamined Patent Application Publication No. 2002-95635) is regarded as a leading technology among them. The scattering spectroscopy and scattering imaging are a technology for finding an early change which is difficult to find on a general observation image by optically capturing the scattering change based on a fact that nucleus and structural variants may cause an optical scattering change.

Conventionally, many propositions each using a polarizing optical system has been made in order to measure and/or image a scattering characteristic of the inner part of epitheliums. While a rear single light scattered from the surface of the epitheliums holds a polarized component, multiple light scattered from the inner layer of the epitheliums (such as a mucous membrane layer or a mucous membrane inner layer) are not polarized. Based on the knowledge and based on differential observation values of the horizontal and vertical polarized components, the scattering characteristic is imaged in the proposed technologies.

By illuminating a living body tissue with observation light polarized in a certain direction (such as the horizontal direction), the rear scattering light from a cell arrangement of the surface of the epitheliums can be observed as a polarized component in the same direction (such as the horizontal direction). On the other hand, the light propagated to the inner part of the epitheliums is not polarized due to the multiple scattering effect because of a structure on a cell and/or various tissues can be observed as scattering light reflected by the surface of the tissue.

By observing the light by using a polarizer in a different direction (such as the vertical direction) from that of the observed light, the magnitude of multiple scattered light can be estimated. The value is used to correct the influence of the multiple scattering included in the observed light (horizontally polarized light) maintaining most polarized light by performing a differential operation and to extract single scattered light from cells of the surface layer of the epitheliums.

The single scattering phenomenon from cells can be modeled as Mie scattering from various spherical particles floating in protoplasm. A characteristic of Mie scattered light is that the scattering spectrum form depends on a size of a scattering particle, a refractive index ratio with respect to a peripheral medium (mainly protoplasm in this case) and a observation wavelength. Especially, the relationship between the particle size and the spectrum form is important.

The particle size of the epithelium of the mucous membrane can be estimated by fitting the spectrum form of the single scattered light extracted by the measurement of the polarized light by using a Mie scattering model and by using different particle sizes and the non-linear least square technique, for example.

A cell nucleus is considered as one of main elements contributing to the scattering in the epitheliums. Therefore, it is considered that the particle size estimated by the technique has a high correlation with the size of the cell nucleus.

Since the above-described nucleus variant involves a nucleus swelling (which means that the size of the nucleus increases from the normal size with the tumor changes), the estimation of the size of the nucleus by using the technique allows the estimation of a state of the tumor change in the epitheliums.

Therefore, spectroscopy using polarized light and imaging have a possibility to image a nucleus swelling.

As described above, the spectroscopy and imaging by using polarized light may image a nucleus swelling quantitatively. However, the application to an endoscope may cause problems below:

A special scope self-containing a polarizing optical system is required;

A highly sensitive image pickup element (an optical element for generating and receiving polarized light) is required because polarized light is used (the light energy extremely decreases when a polarizer is used); and A device is required for obtaining angles of illumination light and observation light (rear scattering angles) precisely in order to model based on Mie scattering (in Mie scattering model, the angle of observed rear scattered light largely depends on the spectrum form).

By overcoming these problems, high-performance scattering imaging apparatus may be achieved. However, the problems still remain from the viewpoint of the cost of the apparatus.

The present invention was made in view of the problems. It is an object of the invention to provide an imaging apparatus which can perform easy scattering imaging only by improving a light source device and the internal part of a processor when an existing endoscopic optical system is used as it is.

DISCLOSURE OF INVENTION

There is provided an imaging apparatus, including a light source device, an image pickup device for converting a living body observed image to video signals by using light irradiated from the light source device for observation, and a processor for generating a living body image from the video signals, wherein the processor has means for generating a living body image having at least a scattering feature of a living body tissue as image information.

The other features and advantages of the present invention will be sufficiently apparent from following descriptions.

BRIEF DESCRIPTION OF THE DRAWINGS

FIG. 1 is a configuration diagram illustrating a configuration of a scattering imaging apparatus; FIG. 2 is a diagram showing a structure of a rotating filter in FIG. 1; FIG. 3 is a diagram showing a spectral characteristic of a rotating filter in FIG. 2; FIG. 4 is a block diagram illustrating a configuration of an image processing circuit in FIG. 1; FIG. 5 is a diagram for describing a mucous membrane tissue of a digestive tube on which the scattering imaging apparatus in FIG. 1 performs scattering imaging; FIG. 6 is a diagram for describing a filter having a spectral characteristic causing a desired scattering characteristic in the mucus membrane tissue of the digestive tube in FIG. 5; FIG. 7 is a diagram for describing an operation of a spectrum estimating portion in FIG. 4; FIG. 8 is a flowchart showing a flow of processing by the spectrum estimating portion in FIG. 4; FIG. 9 is a diagram for describing an operation of a scattering feature calculating portion in FIG. 4; and FIG. 10 is a diagram showing a structure of a variation example of the rotating filter in FIG. 1.

FIG. 12 is a configuration diagram showing a configuration of a scattering imaging apparatus; and FIG. 13 is a diagram showing a structure of a rotating filter in FIG. 12.

FIG. 15 is a configuration diagram showing a configuration of an image processing circuit; FIG. 16 is a first diagram for describing an operation of the image processing circuit in FIG. 15; FIG. 17 is a second diagram for describing an operation of the image processing circuit in FIG. 15; and FIG. 18 is a flowchart for describing an operation of the image processing circuit in FIG. 15.

FIGS. 19 to 23 relate to a sixth embodiment of the present invention. FIG. 19 is a configuration diagram showing a configuration of an image processing circuit; FIG. 20 is a first diagram for describing an operation of the image processing circuit in FIG. 19; FIG. 21 is a second diagram for describing an operation of the image processing circuit in FIG. 19; FIG. 22 is a third diagram for describing an operation of the image processing circuit in FIG. 19; and FIG. 23 is a flowchart for describing an operation of the image processing circuit in FIG. 19.

BEST MODE FOR CARRYING OUT THE INVENTION

The present invention will be described in detail with reference to attached drawings.

First Embodiment

Figure 1:
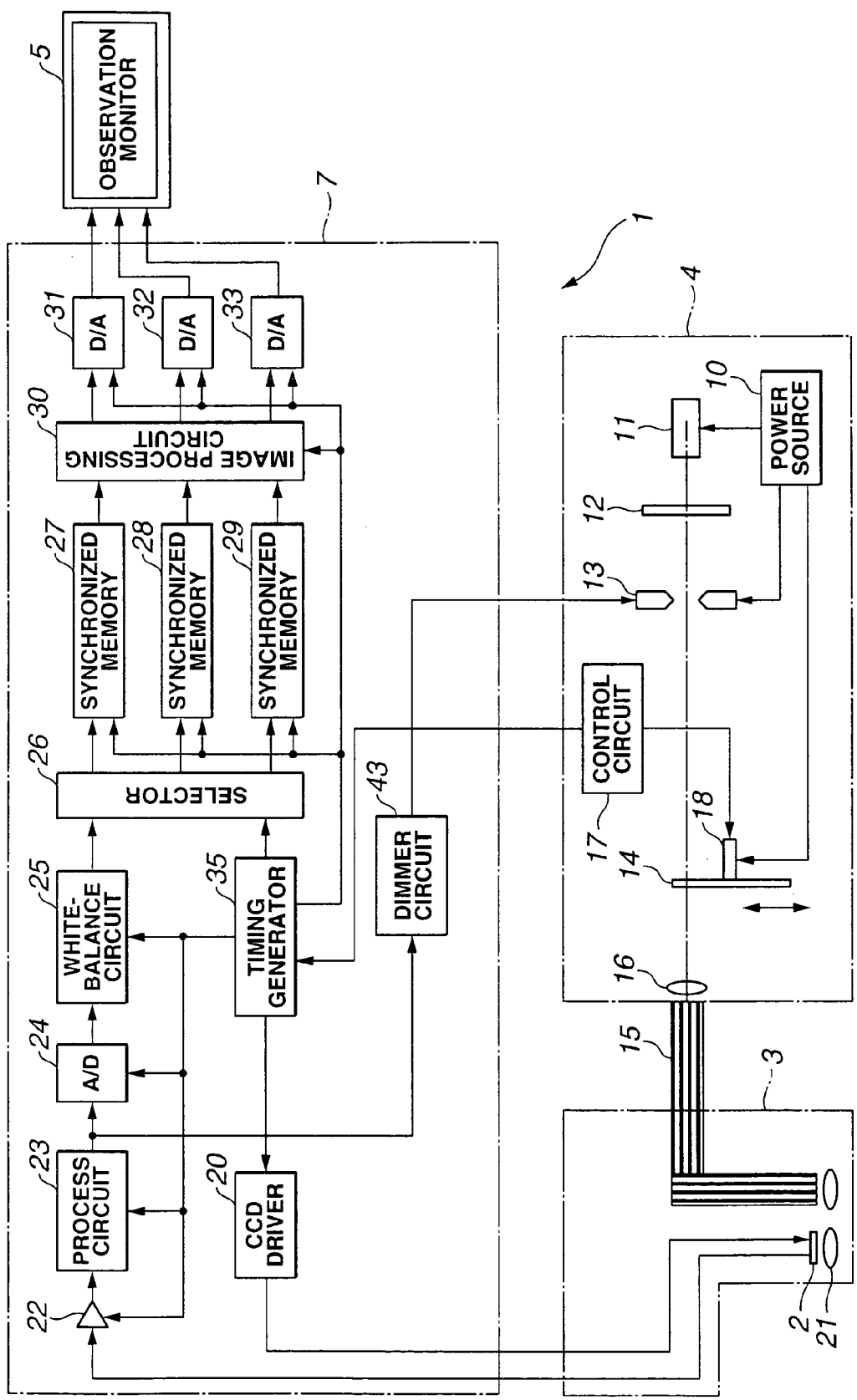
FIGS. 1 to 10 relate to a first embodiment of the present invention.

As shown in FIG. 1, an endoscopic device 1 included in a scattering imaging apparatus according to this embodiment includes an electronic endoscope 3 having a CCD 2 as image pickup means to be inserted into a body cavity for picking up an image of a tissue in the body cavity, a light source device 4 for supplying illumination light to the electronic endoscope 3, and a video processor 7 for signal-processing image pickup signals from the CCD 2 of the electronic endoscope 3 and displaying an endoscopic image on an observation monitor 5.

The light source device 4 includes a xenon lamp 11 for emitting illumination light, a heat ray cut filter 12 for shielding heat rays of white light, an aperture device 13 for controlling a light amount of white light through the heat-ray cut filter 12, a rotating filter 14 for changing illumination light to field sequential light, a condensing lens 16 for gathering field sequential light through the rotating filter 14 onto an incident plane of a light guide 15 disposed in the electronic endoscope 3, and a control circuit 17 for controlling the rotation of the rotating filter 14.

Figure 2:
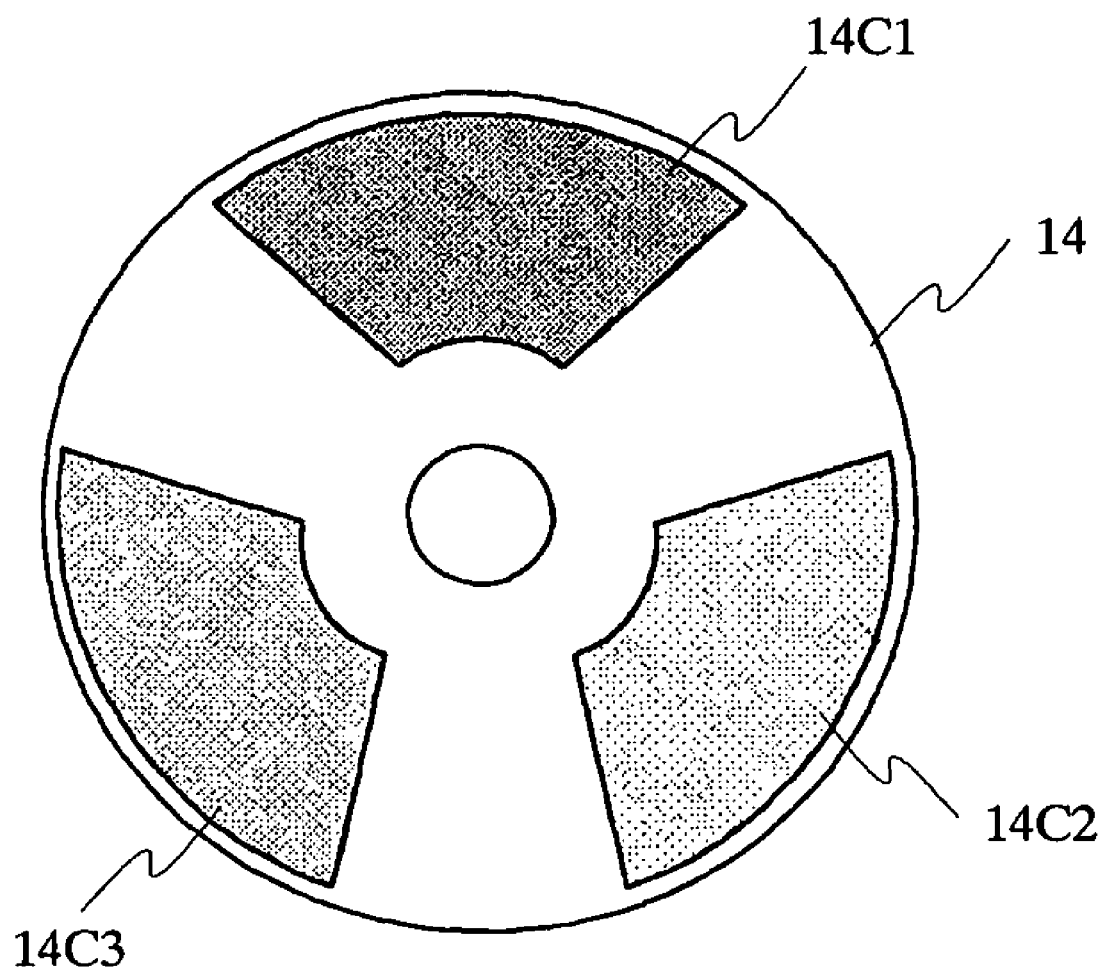
Figure 3:
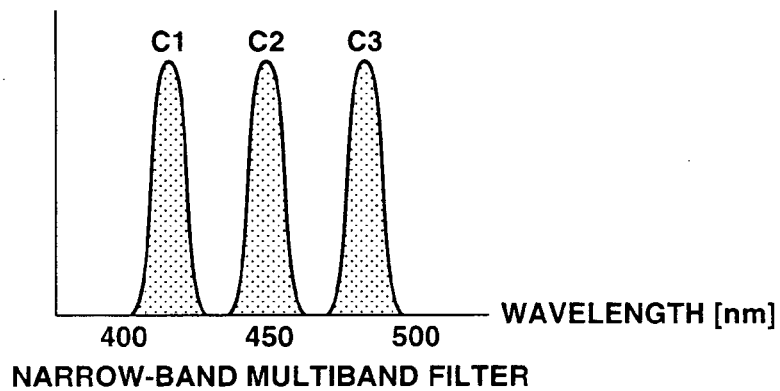

As shown in FIG. 2, the rotating filter 14 has a disk shape and rotates about the center. The rotating filter 14 has a filter set of a C1 filter 14c1, C2 filter 14c1 and C3 filter 14c1 for outputting field sequential light having spectral characteristic as shown in FIG. 3. As shown in FIG. 1, a rotating filter motor 18 is drive-controlled by the control circuit 17 so that the rotating filter 14 can rotate.

Power is supplied from a power source portion 10 to the xenon lamp 11, the aperture device 13 and the rotating filter motor 18.

Referring back to FIG. 1, the video processor 7 includes a CCD driving circuit 20, an amplifier 22, a process circuit 23, an A/D converter 24, a white-balance circuit 25, a selector 26, synchronized memories 27, 28 and 29, an image processing circuit 30, D/A circuits 31, 32 and 33, a timing generator 35, and a dimmer circuit 43. The CCD driving circuit 20 drives the CCD 2. The amplifier 22 amplifies image pickup signals which pick up the image of a tissue in a body cavity by using the CCD 2 through an objective optical system 21. The process circuit 23 performs correlation double sampling and noise removal on image pickup signals having passed through the amplifier 22. The A/D converter 24 converts the image pickup signals having passed through the process circuit 23. The white-balance circuit 25 performs white-balance processing on image data from the A/D converter 24. The selector 26 and the synchronized memories 27, 28 and 29 are used for synchronize field sequential light by the rotating filter 14. The image processing circuit 30 performs reading gamma correction processing, contour emphasis processing, color processing and so on on image data of field sequential light stored in the synchronized memories 27, 28 and 29. The D/A circuits 31, 32 and 33 convert image data from the image processing circuit 30 to analog signals. The timing generator 35 inputs synchronization signals in synchronization with a rotation of the rotating filter 14 from the control circuit 17 of the light source device 4 and outputs different kinds of timing signals to the respective circuits. The dimmer circuit 43 inputs image pickup signals having passed through the process circuit 23, controls the aperture device 13 of the light source device 4 and performs proper brightness control.

Figure 4:
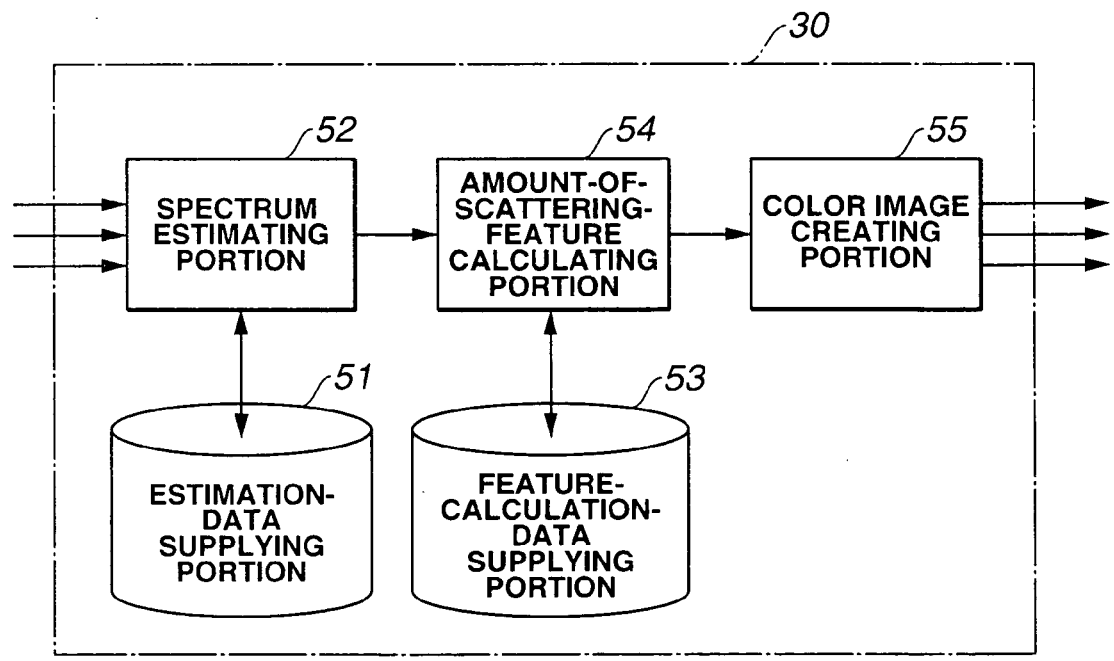

As shown in FIG. 4, the image processing circuit 30 includes a spectrum estimating portion 52, a scattering feature calculating portion 54, and a color image creating portion 55. The spectrum estimating portion 52 estimates a spectrum of respective pixels by inputting image data from the synchronized memories 27, 28 and 29 and obtaining data required for the spectrum estimation from an estimation data supplying portion 51. The scattering feature calculating portion 54 calculates several scattering features based on the spectrum of respective pixels from the spectrum estimating portion 52 and data required for feature calculation from the feature calculation data supplying portion 53. The color image creating portion 55 calculates a display color based on a scattering feature image from the scattering feature calculating portion 54 and determines an RGB value of respective pixels so as to display a scattering feature as a color image. Thus, the color image creating portion 55 outputs the RGB values as an RGB image to the D/A circuits 31, 32 and 33.

The estimation data supplying portion 51 and the feature calculation data supplying portion 53 are provided in the video processor 7 or in an external block.

Figure 5:
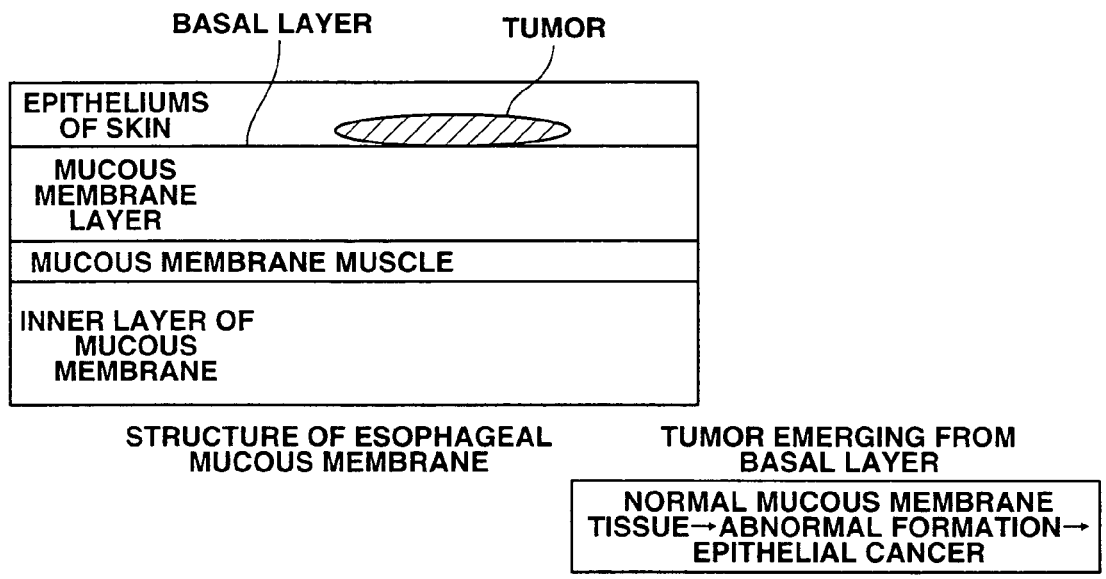

A mucous membrane tissue of a digestive tube such as the esophagus almost has a structure as shown in FIG. 5. A tumor such as an esophageal cancer emerges from a basal layer separating the epitheliums and the mucous membrane layer. The tumor emerging from the basal layer has a nucleus variant and a structure variant and replaces the entire of epitheliums by variant cells. Then, the tumor advances to a cancer through a so-called variant forming state.

The epitheliums include a flat epithelium and exhibit a strong scattering characteristic due to the hard-grained cell structure. The scattering characteristic has a wavelength dependence and may have a characteristic that the scattering characteristic decreases from the short wavelength to the long wavelength (therefore, it is considered that most of light with a short wavelength is scattered and reflected in the epitheliums and the deeper transmission to the mucous membrane layer and lower layers may be less.)

Accordingly, in order to capture a change in scattering characteristic within epitheliums, short-wavelength light is more suitable than long-wavelength light. This is true for imaging, and narrow band multiband illumination will be described, for example.

Figure 6:
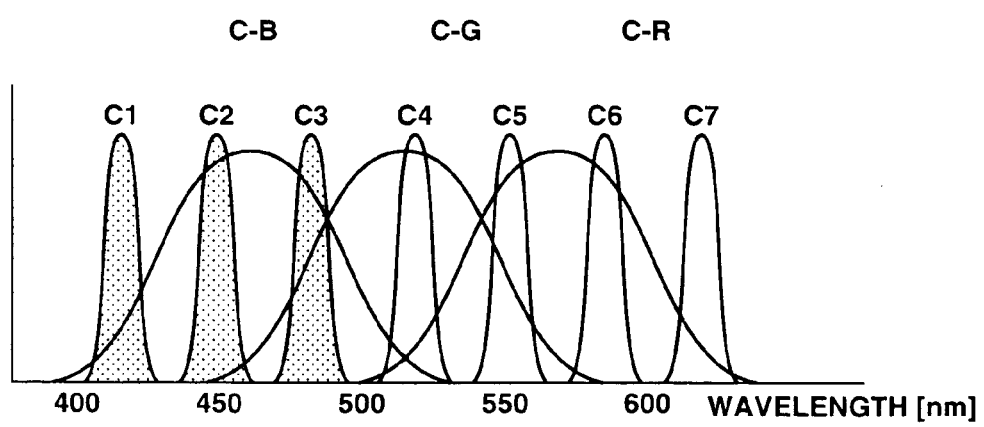

As shown in FIG. 6, in order to naturally reproduce colors in a rotating filter for generating field sequential light, combinations of wide band filters such as C-B, C-G and C-R are generally used. The rotating filter rotates fast so that three band lights can illuminate an object chronologically and sequentially images the object by using a monochrome CCD. The images are synthesized by a video processor, and the band images corresponding to the respective illumination lights are assigned to Blue, Green and Red channels of an observation monitor. Thus, one color image is displayed.

If a filter having a desired characteristic can be produced, the contrast of an image of the blood vessel can be improved by changing the half-value breadth to a narrow band without a large change in center wavelength of the C-B, C-G and C-R such as C2, C4 and C6.

However, the rotary filter 14 selects bands from short-wavelength light here as described above for scattering imaging within the epitheliums. C1, C2 and C3 in FIG. 6 correspond thereto. The multiple band images with shorter wavelengths may show a structure within the epitheliums better than those of bands (C4, C5, C6 and C7) with longer wavelengths.

Here, the band images corresponding to C1, C2 C3 illumination lights may be assigned to the Blue, Green and Red channels so that one color image can be reproduced therefrom on an observation monitor. However, what kind of scattering characteristic the color information corresponds to and what kind of pathological change (such as a degree of a structural variant and a degree of a nucleus swelling) the color change corresponds to are not clear, and understanding the image is not easy. Furthermore, even when a doctor using an endoscope observes such an image during an examination, it is difficult for the observation to contribute to the early discovery of a tumor.

According to this embodiment, a spectral reflectance is estimated from these multiple band images, and a change in feature amount in an image is displayed as color information by converting the estimated spectral reflectance to a feature having higher pathological correlation based on an optical model of a living body tissue.

It is an object of this embodiment to estimate spectral reflectances of pixels from a narrow band multiband image, estimate a feature amount having higher pathological correlation based on an optical model and generate color information based on a change in the estimated feature amount in an image.

[Operation]

Narrow-band band images (for example, three band corresponding to the short wavelength bands, C1, C2 and C3, as shown in FIG. 6) output from the synchronized memories 27, 28 and 29 are input to the spectrum estimating portion 52 provided in the image processing circuit 30. The spectrum estimating portion 52 obtains data required for the spectrum estimation from the estimation data supplying portion 51 within the image processing portion or in an external block. Thus, the spectrum estimating portion 52 estimates the spectrum of each pixel.

The estimated spectrums, that is, the spectrum images are values to be input to the scattering-feature calculating portion 54. The scattering-feature calculating portion 54 obtains data required for the feature calculation from the feature-calculation data supplying portion 53 provided in the image processing portion or in the external block. Thus, the scattering feature calculating portion 54 calculates several scattering features. At this time, several scattering features are assigned to the respective pixels.

The scattering-feature calculating portion 54 outputs the scattering feature images to the color image generating portion 55. The color image generating portion 55 performs a display color calculation based on the scattering feature images. Then, in order to display scattering features as a color image, RGB values of the respective pixels are determined and are output to the D/A circuits 31, 32 and 33 as the RGB images.

Next, an operation in each of the blocks (including the spectrum estimating portion 52, the scattering-feature calculating portion 54 and the color image creating portion 55) will be described. The detail is disclosed in a document, "V. Backman, R. Gurjar, K. Badizadegan, I. Itzkan, R. R. Dasari, L. T. Perelman, and M. S. Feld, 'Polarized Light Scattering Spectroscopy for Quantitative Measurement of Epithelial Cellular Structures In Situ,' IEEE J. Sel. Top. Quantum Electron, 5, 1019-1026 (1999)". In equations below, the symbol, "^" indicates a vector (with a lowercase letter) and matrix (with an uppercase letter) having several elements.

[Spectrum Estimating Portion 52]

A relationship between object spectral reflectances and pixel values of multiband images is represented by EQ1, which is an imaging equation:

$$g^\wedge = H^\wedge f^\wedge + n^\wedge \quad (1)$$

$$g^\wedge = \begin{bmatrix} g_{c1} \\ g_{c2} \\ g_{c3} \end{bmatrix},$$

$$H^\wedge = \begin{bmatrix} h_{11} & h_{12} & \cdots & h_{1L} \\ h_{21} & h_{22} & \cdots & h_{2L} \\ h_{31} & h_{32} & \cdots & h_{3L} \end{bmatrix},$$

$$f\hat{} = \begin{bmatrix} f_1 \\ f_2 \\ \vdots \\ f_L \end{bmatrix},$$

$$n\hat{} = \begin{bmatrix} n_{c1} \\ n_{c1} \\ n_{c2} \end{bmatrix}$$

Here, g^ is a pixel value column vector having dimensions (N: three in this embodiment) the number of which is equal to the number of bands. f^ is an object spectral reflectance column vector, and the value is discrete at L in the wavelength direction. n^ is a noise column vector. H^ is a system matrix of L×N having N row vectors, which is a spectral sensitivity characteristic of each band.

The problem is that H^ is known and the spectral reflectance of an object is estimated from the observation value g^. H^ is known as spectral characteristics of an imaging system, such as an observation light spectrum, a spectral transmittance characteristic of a narrow band filter and a spectral sensitivity characteristic of an image pickup element.

In general, since "number of bands N<number of samplings L", the estimation problem is ill-condition. That is, an infinite number of f^ satisfying EQ1 exist for g^. (In other words, since the number of equations is lower than the number of unknown values, various solutions are possible. Therefore, one solution cannot be determined as far as some condition is given).

By preparing foresight information and limiting a solution space (L-dimensional spectrum space in this case), (this would be a condition to determine one exclusive solution), an appropriate estimated solution must be found. That is, it is concluded in a problem for obtaining an optimum solution within a partial space, of the L-dimensional spectrum space by using foresight information, in which spectrums distribute candidates of the solution.

Wiener estimation is generally used as a technique using foresight information. EQ2 represents an estimation matrix A in Wiener estimation. By multiplying the estimation matrix A from the right of the observation vector g, the spectrum is estimated. Therefore, the spectrum estimating means operates as a matrix calculator using the predefined estimation matrix A.

$$A\hat{} = R_f\hat{} H\hat{}^\tau (H\hat{} R_f\hat{} H\hat{}^\tau + R_n\hat{})^{-1} \quad (2)$$

Here, $R_f\hat{}$ is an auto-correlation matrix (L×L) in the wavelength direction of the object spectrum to be estimated, and $R_n\hat{}$ is an auto-correlation matrix of additive noise appearing as n^ in EQ1. $R_n\hat{}$ can be estimated from the pre-measured noise characteristic of an imaging system (which is a total system having a combination of a light source and a scope) and is known. The foresight information here is $R_f\hat{}$ and $R_n\hat{}$. Especially, $R_f\hat{}$ is the most important parameter influencing on the validity of the spectral reflectance to be estimated.

Conventionally, the opposite of a differential operator matrix (that is, low-frequency enhancing filter in a space frequency area) is often used as the auto-correlation matrix $R_f\hat{}$ given that the spectrum to be estimated is smooth in the wavelength direction (that is, the spectrum has a smoother characteristic in the wavelength direction without rapid changes in wavelength unlike an emission spectrum). Alternatively, a Marcov transition matrix is often used as the auto-correlation matrix $R_f\hat{}$ since the spectral reflectance can be represented by a statistics model such as Marcov model.

According to this embodiment, an auto-correlation matrix is used which is obtained from a spectrums estimated from a discrete particle structure model (which is called optical model hereinafter and will be described as the auto-correlation matrix $R_f\hat{}$ later) of a living body tissue.

Next, the optical model will be described. A living body tissue includes various elements such as a fiber tissue, cells, lymphocytes, capillary tubes, nucleuses and small organs within each cell.

Since a scattering occurs at an area having a large change in refractive index, a main scattering body (scattering entity) in the living body tissue is considered to be a small organ within a cell such as a nucleus and mitochondria. The phase function and scattering coefficient of a particle having a wavelength equivalent to or a little smaller than the observation wavelength can be estimated by using the Mie scattering model. The phase function represents a probability of the scattering of light incident on the scattering entity from a direction s to a direction s'. The scattering coefficient is a parameter indicating the number of times that a photon is subject to scattering for every distance unit.

The Mie model has 2πma/λ as a parameter of the model (where λ is a wavelength, m is a refractive index ratio and a is a diameter of the scattering entity. Since the refractive index ratio between the nucleus and the protoplasm may not have a large change, Mie scattering can be a model for estimating a scattering spectrum by mainly using the scattering entity as a parameter.

Figure 7:
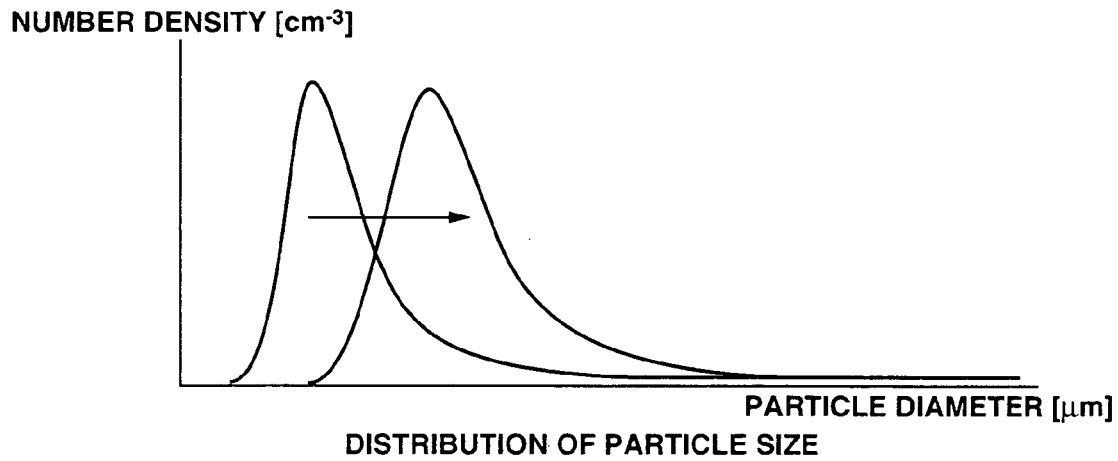

On the other hand, from the information (particle size distribution function) of the size and density of particles (such as nucleuses and small organs in cells) in the living body tissue, the phase function and scattering coefficient can be estimated by using the Mie scattering model. FIG. 7 shows a conceptual diagram of a particle size distribution. An actual diameter of a particle is considered to be in the range from about 0.4 μm for a small organ within a cell to about 4 μm for a nucleus. As the structure variant advances from the normal tissue, the particle size distribution is considered to change (f1(d) to f2(d) where d is a particle diameter) as indicated by an arrow in FIG. 7. The phase function and the scattering coefficient are calculated by using the Mie scattering model based on the particle size distribution function and the refractive index rate between a particle and a peripheral medium (about 1.03 where the peripheral medium should be protoplasm). The particle size distribution function can be applied to a normal distribution and/or a logarithm normal distribution. An optical coefficient is calculated from the Mie scattering model for a change in particle size distribution parameter (such as a mean and a standard deviation), which is conceivable for a target. A spectrum is calculated by simulating a multiple scattering process by using a light propagation model based on the calculated optical coefficient.

The light propagation model may be a method using a scattering equation which is advantageous in calculation time as an analytical method but has a large limitation in degree of freedom in model shape. Alternatively, the light propagation model may be Montecarlo model requiring a time for the calculation but having a higher degree of freedom in model form. In this way, different kinds of methods can be used in accordance with the condition.

Figure 8:
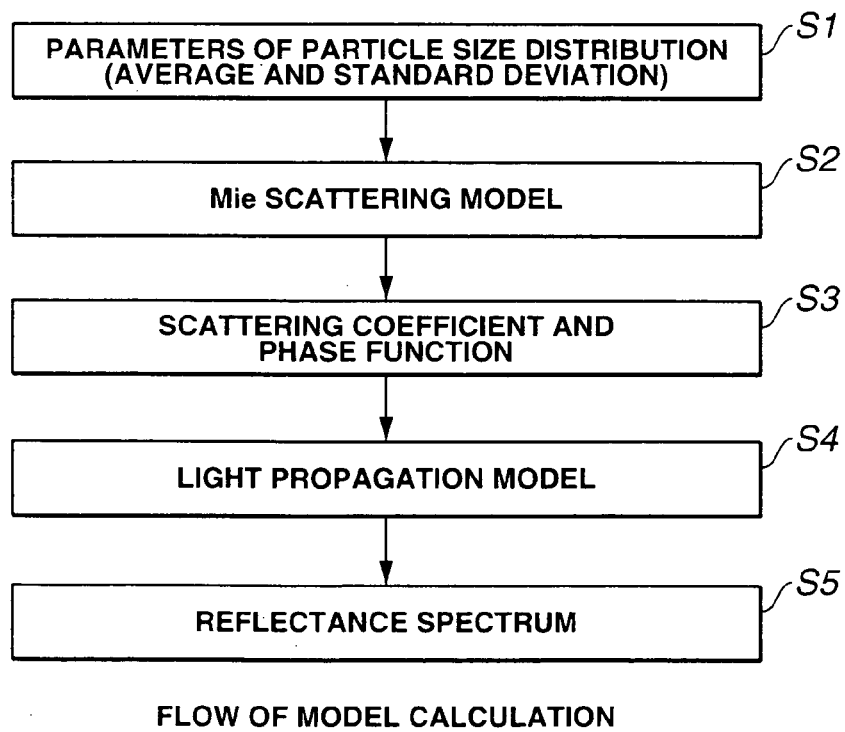

Summing up the model calculation up to this point, as shown in FIG. 8, particle size distribution parameters (including a mean and a standard deviation) are obtained at a step S1. The particle size distribution parameters are input to Mie scattering model at the step S2. At a step S3, a scattering coefficient and a phase function are output from the Mie scattering model. In reality, the scattering coefficient and the phase function are calculated by applying the Mie scattering model for every size of each particle. Then, a Mie scattering calculation in consideration of the particle size distribution by using the particle size as a weighted sum mean, which is a weight function.

Through the model calculation, a spectrum is calculated by using a nucleus variant and structure variant with the tumor change within epitheliums as changes in particle size distribution parameters (mean and standard deviation). Then, a solution space (spectrum space) is limited by using the spectrum as preliminary information. In other words, the auto-correlation matrix $R_f$ in Wiener estimation is calculated in advance from the spectrum distribution estimated from the model calculation.

More specifically, at a step S4, a spectrum change in accordance with changes in particle size distribution parameters (changes in mean and standard deviation) obtained from the pathological information is calculated by using Mie scattering model and a light propagation model. As a result of the calculation, a spectrum distribution in accordance with the changes in particle size distribution parameters is formed in a spectrum space at a step S5. By using the spectrum distribution as a population, the auto-correlation matrix in the wavelength direction of the spectrum is estimated.

As described above, the scattering spectrum within the epitheliums is estimated by using the auto-correlation matrix estimated in advance from the optical model (particle size distribution model+Mie scattering model+light propagation model). Therefore, the matrix A to be calculated by EQ2 based on $H^\wedge$, $R_f^\wedge$ and $R_n^\wedge$ is stored in the estimation data supplying portion.

[Scattering Feature Calculating Portion 54]

Figure 9:
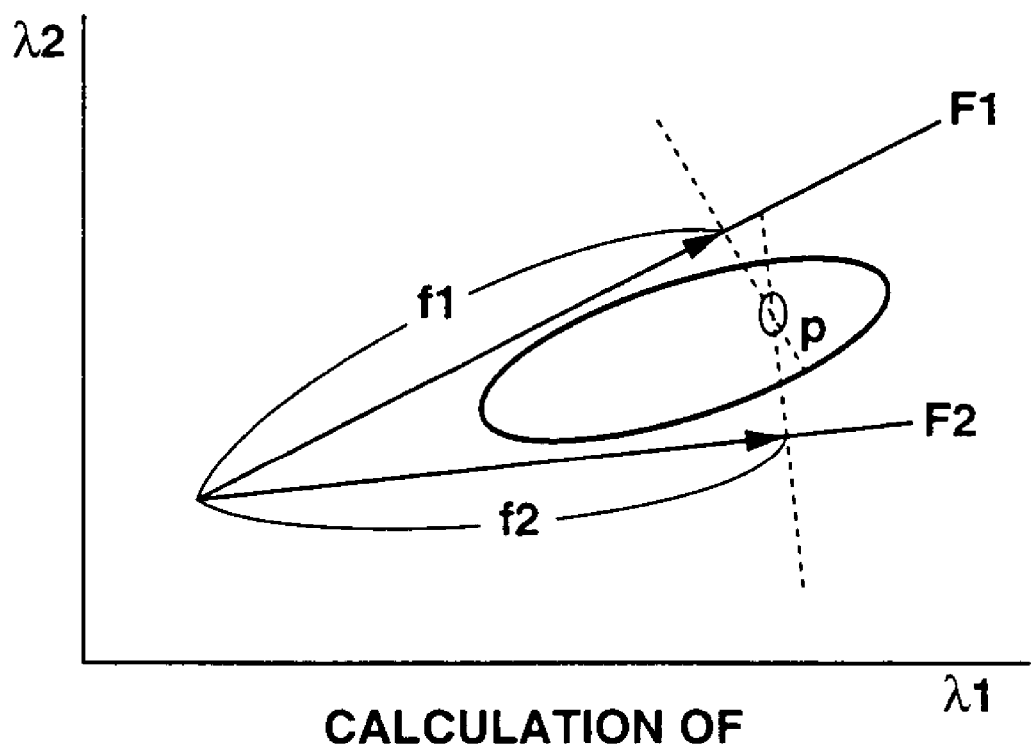

Various features can be calculated from the spectrum estimated by the spectrum estimating portion 52. This embodiment focuses on the particle size distribution parameters and proposes a method for estimating a feature amount correlated to the parameters from the spectrum. FIG. 9 shows a conceptual diagram thereof.

When the auto-correlation matrix is estimated, a spectrum change range for the changes in particle size distribution parameters (including mean and standard deviation) are known.

Therefore, feature axes corresponding to the mean and standard deviation, which is considered to be scattering features, are known as F1 and F2. In other words, spectrums are distributed in a partial space which locates between F1 and F2. Thus, from the calculated spectrum, scattering features are obtained including projection values (f1 and f2) to F1 and F2 and the brightness (such as an area of the spectrum) as a third value. Therefore, spectrums of the feature axes are stored in the feature calculation data supplying portion. The calculation in the calculating portion is an inner product calculation of a feature axis spectrum and a scattering spectrum.

[Color Image Generating Portion 55]

A color image is generated by assigning the scattering features and the spectrum brightness output from the scattering feature calculating portion 54 to the Blue, Green and Red channels. Here, the pixel values must be properly quantized to 8 bits, for example, in accordance with the D/A performance of a downstream unit. In order to discover a change at an early stage on a screen, the relative scattering changes, that is, the degrees of the nucleus variant and structure variant may be only required. Therefore, in a frame, the scattering features are quantized at a predetermined level such as 8-bits by calculating the dynamic range and are output as RGB signals.

Summing up the characteristics of this embodiment, a scattering spectrum is estimated by using a multiband image in a short wavelength range, which is conceivable as having a lower invasive degree and strongly reflecting features of the inside of the epitheliums and an auto-correlation matrix estimated from a model-based spectral reflectance distribution calculated from a Mie scattering model and a light propagation model by modeling the epithelial tissue as a discrete particle structure. The projection values to feature axes corresponding to pre-calculated particle size distribution parameters in a spectrum space are used as scattering features. Then, the amounts of these features for each pixel are assigned to color channels, and the scattering imaging is achieved by using the color information.

[Advantages]

According to this embodiment, an imaging correlated to changes in scattering characteristic is allowed by performing calculations in a narrow-band filter and a processor without a special scope such as a polarizing optical system. Thus, this embodiment allows the visual recognition of a feature such as a structure variant within epitheliums, which cannot be observed easily before.

Figure 10:
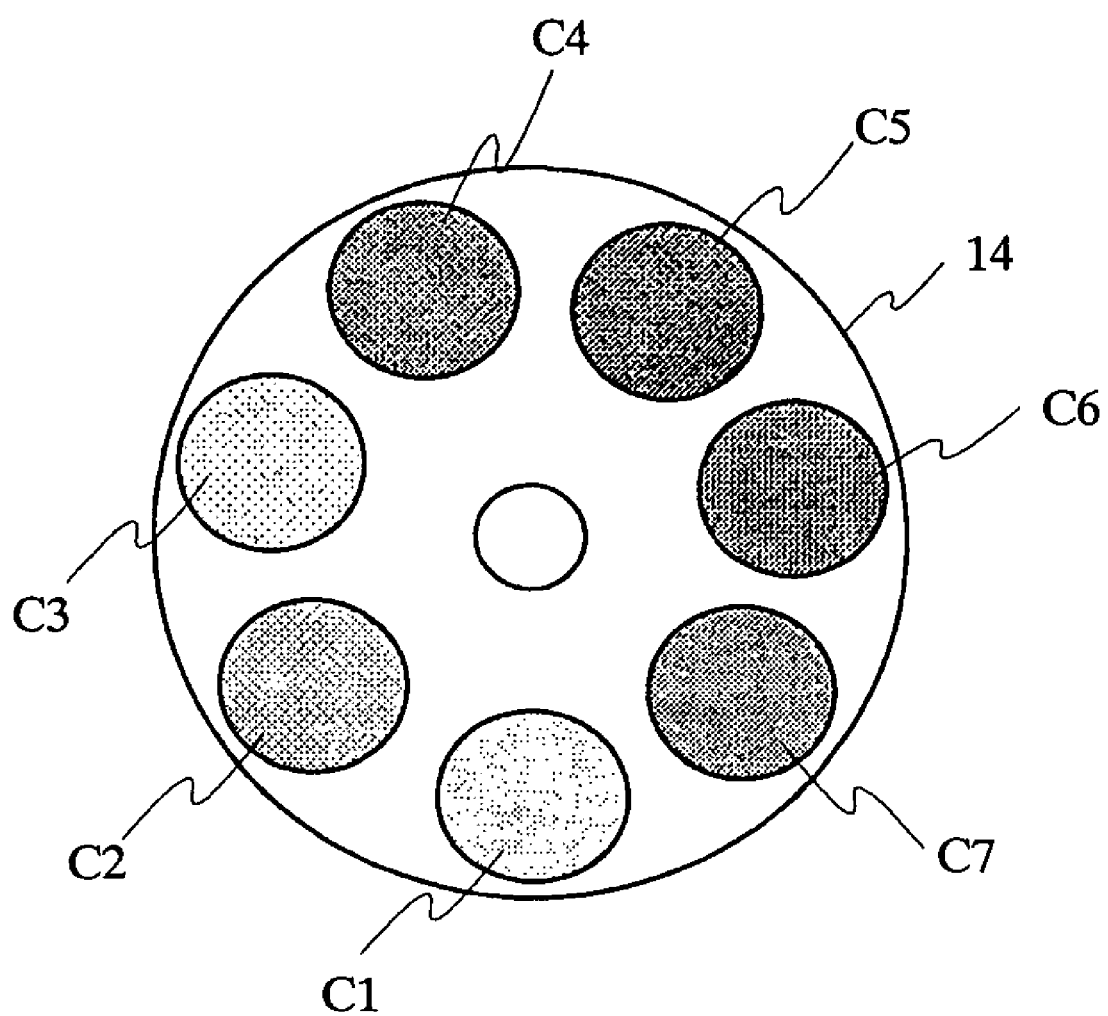

In order to obtain a general observation image, the rotating filter 14, as shown in FIG. 10, having narrow-band filters 14C1 to C6 for the multiple narrow bands C1 to C6 (see FIG. 6) may be used. In this case, memories number of which is equal to the number of filters are provided for respective images of the narrow-band filters. Furthermore, in this case, the image processing circuit 30 includes a general observation image generating portion and the spectrum estimating portion 52+the scattering feature calculating portion 54 (not shown) according to the first embodiment. The image processing circuit 30 further includes a contrast enhancing coefficient calculating portion for calculating an enhancement coefficient based on an output of the scattering feature calculating portion 54. A quantized value is calculated based on a value correlated to a synthesized feature using a mean or a standard deviation and mean of a particle size distribution, for example, within a frame. Based on the value, an enhancement coefficient of a space frequency is calculated for a luminance channel of an image generated by the general observation image generating portion. Thus, the contrast enhancement can be performed on the general observation image based on the scattering features.

Second Embodiment

Since a second embodiment is substantially the same as the first embodiment, only differences therebetween will be described. The same reference numerals are given to the same components as those of the first embodiment, and the description will be omitted here.

[Structure and Operation]

In order to estimate a scattering spectrum in epitheliums, multiple narrow-band filter is used in a short-wavelength area. The band has a strong scattering characteristic while the band has a maximum absorption (415 nm) of hemoglobin. For example, an esophagus flat epithelium does not have capillary tubes in the normal mucous membrane. With the swelling of a nucleus, the blood vessel within a nipple may expand and/or a vascularity may occur within the epitheliums. This kind of capillary tube image has a unique spectrum due to hemoglobin, which may become an error factor in the scattering spectrum estimation. Therefore, the capillary tube image as an absorption image is separated before the scattering spectrum estimation.

Figure 11:
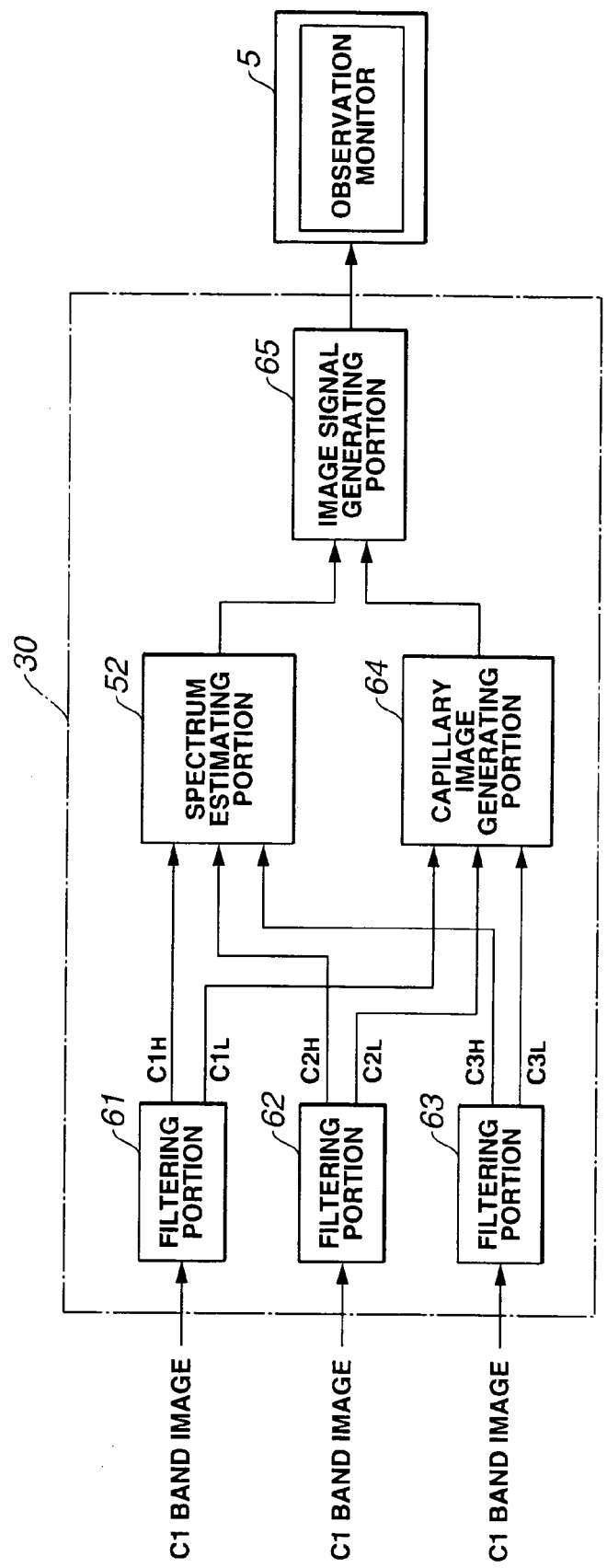
FIG. 11 is a block diagram showing a configuration of an image processing circuit according to a second embodiment of the present invention.

For the separation, the facts are considered that these capillary tube images dynamically have high spatial frequency and that a scattering image itself forms a low frequency image due to multiple scatterings. More specifically, as shown in FIG. 11, the image processing circuit 30 according to this embodiment includes filtering portions 61, 62 and 63 corresponding to narrow-band band images by spatial frequency filter before the scattering spectrum estimating portion 52. The operations by the filtering portions 61, 62 and 63 can be performed by a convolution computer having an FIR filter. The convolution computer includes a high frequency band pass filter for separating capillary tube images and a low pass filter for estimating scattering spectrums.

Outputs from the filtering portions 61, 62 and 63 corresponding to the respective narrow-band band images are separated into high frequency images C1H, C2H and C3H (where H is a subscript) and low frequency images C1L, C2L and C3L (where L is a subscript) corresponding to the respective band images. The low frequency images are output to the scattering spectrum estimating portion 52. The high frequency images are output to capillary tube image generating means 64.

As described in the first embodiment, the scattering spectrum estimating portion 52 estimates a scattering spectrum by calculating an auto-correlation matrix in Wiener estimation from a rear scattering spectrum distribution within the epitheliums, which is estimated from a discrete particle structure model.

On the other hand, the capillary tube image generating portion 64 generates a capillary tube image more clearly by properly removing noise from and, in some cases, using a matched filter modeling a blood vessel structure for the high frequency images generated from the bands. Then, the capillary tube images are output to an image signal generating portion 65 as luminance information.

The image signal generating portion 65 generates a scattering characteristic by using a color map based on the output from the scattering spectrum estimating portion 52 and synthesizes the capillary tube images as luminance information. Thus, the image signal generating portion 65 outputs the scattering+capillary tube absorption images to an observation monitor 5.

[Advantages]

According to this embodiment, an imaging correlated to changes in scattering characteristic is allowed by performing calculations in a narrow-band filter and a processor without a special scope such as a polarizing optical system. Thus, this embodiment allows the visual recognition of a feature such as a structure variant within epitheliums, which cannot be observed easily before. By separating capillary tube images, which are absorption images, in advance by using spatial filtering means, the decrease in estimation precision of spectral reflectance can be prevented. At the same time, the capillary tube pattern and scattering images, which are important for discrimination diagnosis, can be synthesized and displayed.

Third Embodiment

A third embodiment is substantially the same as the first embodiment. Therefore, only the differences therebetween will be described. The same reference numerals are given to the same components, and the descriptions will be omitted.

[Structure and Operation]

Figure 13:
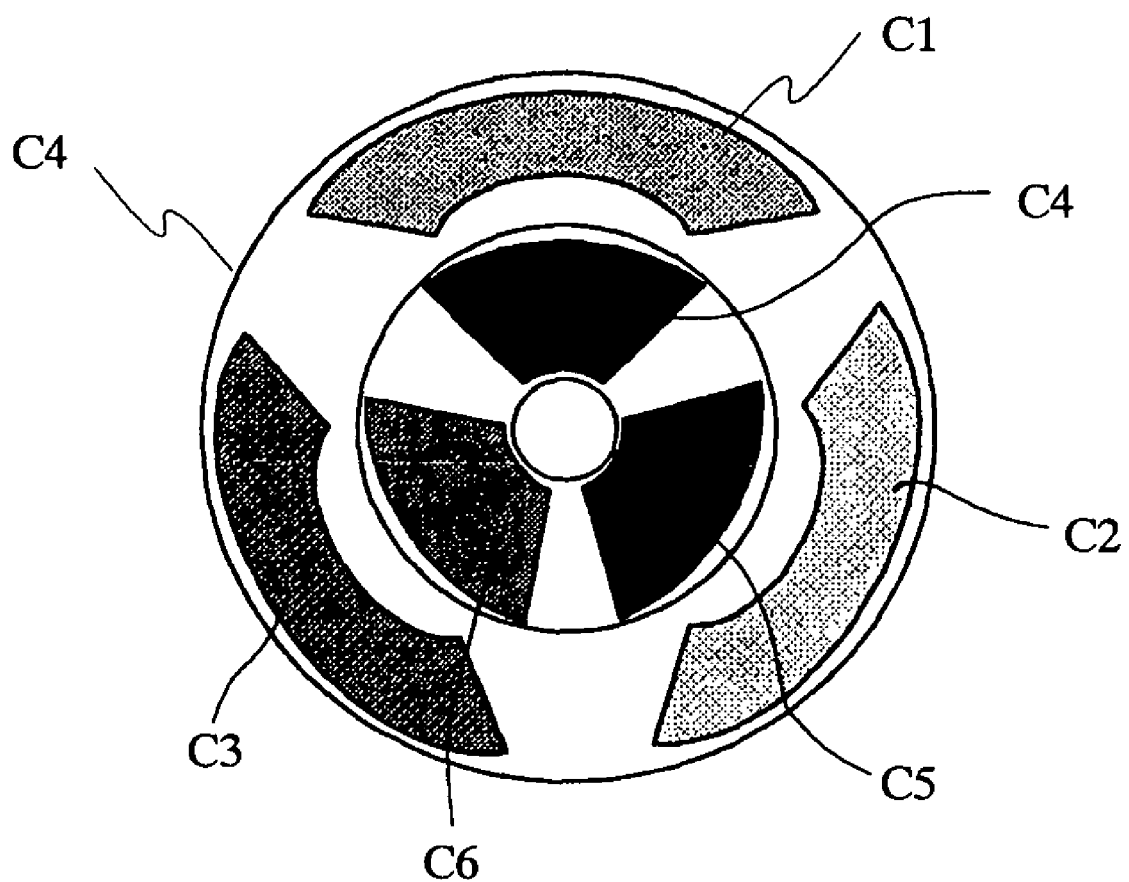

As shown in FIG. 13, the rotating filter 14 according to this embodiment has a disk shape and has a double structure rotatably about the center. A first filter set including a C1 filter 14C1, a C2 filter 14C2 and a C3 filter 14C3 for outputting narrow band field sequential light having spectral characteristics indicated by C1 to C3 shown in FIG. 6 are disposed on the outer diameter part. A second filter set including a C4 filter 14C4, a C5 filter 14C5 and a C6 filter 14C6 for outputting field sequential light having spectral characteristics indicated by C4 to C6 shown in FIG. 6 are disposed on the inner diameter part.

Figure 12:
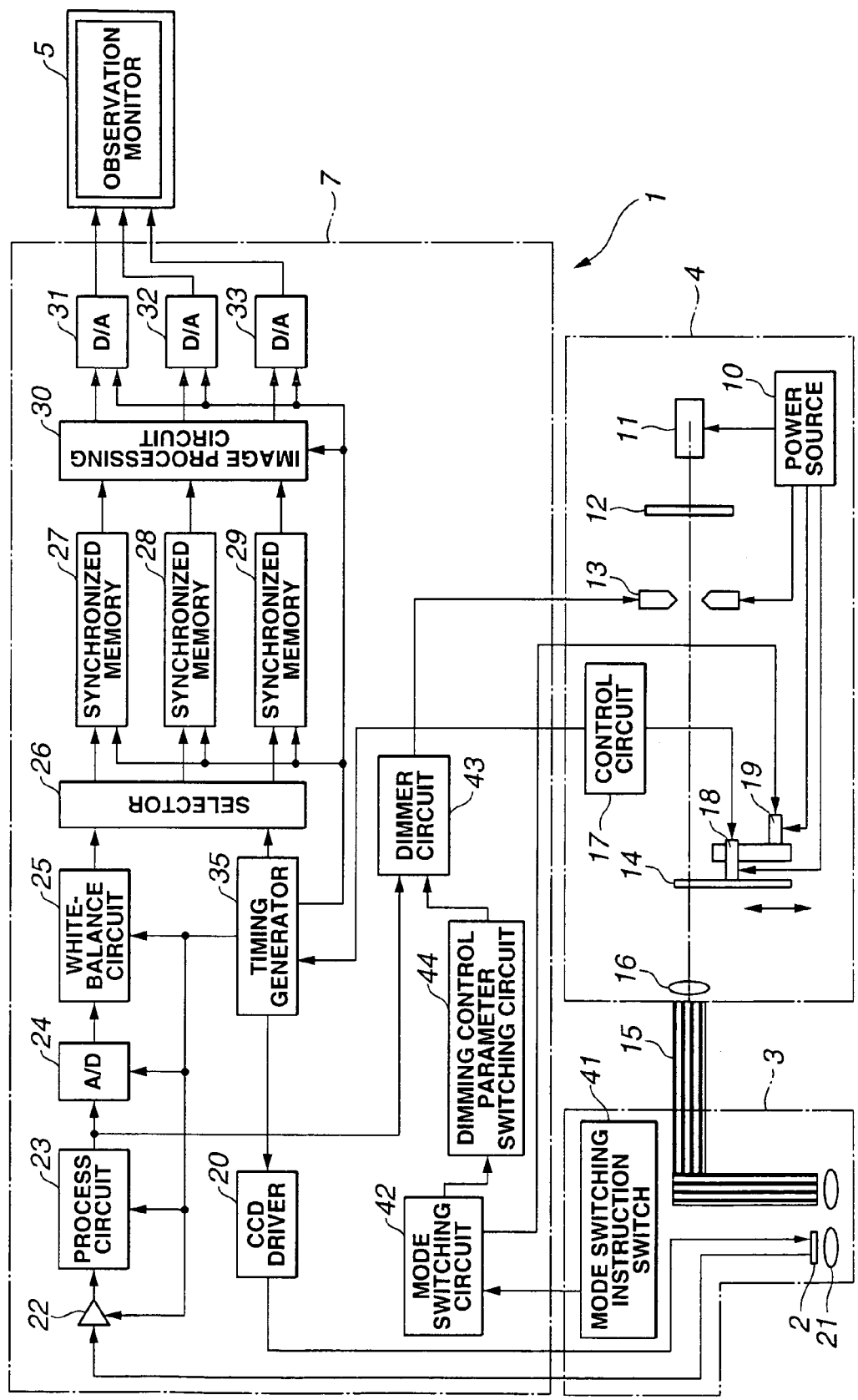
FIGS. 12 and 13 relate to a third embodiment of the present invention.

As shown in FIG. 12, the rotating filter 14 is rotated under the driving control of the rotating filter motor 18 by the control circuit 17. The movement in the diameter direction (which is movement vertical to an optical path of the rotating filter 14 and selectively moves the first filter set or second filter set of the rotating filter 14 on the optical path) is performed by a mode switching motor 19 in accordance with a control signal from a mode switching circuit 42 in the video processor 7.

Power is supplied from the power source portion 10 to the xenon lamp 11, the aperture device 13, the rotating filter motor 18 and the mode switching motor 19.

The electronic endoscope 2 includes a mode select switch 41. The output of the mode select switch 41 is output to the mode switching circuit 42 in the video processor 7. The mode switching circuit 42 in the video processor 7 outputs control signals to the dimmer circuit 43, a dimming control parameter switching circuit 44 and the mode switching motor 19 of the light source device 4.

The dimming control parameter switching circuit 44 outputs a dimming control parameter in accordance with the first filter set or second filter set of the rotating filter 14 to the dimmer circuit 43. The dimmer circuit 43 controls the aperture device 13 of the light source device 4 based on the control signal from the mode switching circuit 42 and the dimming control parameter from the dimming control parameter switching circuit 44. Thus, the brightness is controlled properly.

[Advantages]

According to this embodiment, in addition to the advantages of the first embodiment, the observation in a body cavity with general observation light can be performed by using the C4 filter 14C4, the C5 filter 14C5 and the C6 filter 14C6.

Fourth Embodiment

Since a fourth embodiment is substantially the same as the first embodiment, only differences therebetween will be described. The same reference numerals are given to the same components, and the description will be omitted here.

[Structure and Operation]

According to the above-described embodiments, an image pickup device is provided within an endoscope, and scattering imaging of a tissue within a body cavity is performed. According to this embodiment, a scattering imaging apparatus will be described which can irradiate narrow band light on a body surface and can detect a skin cancer.

Figure 14:
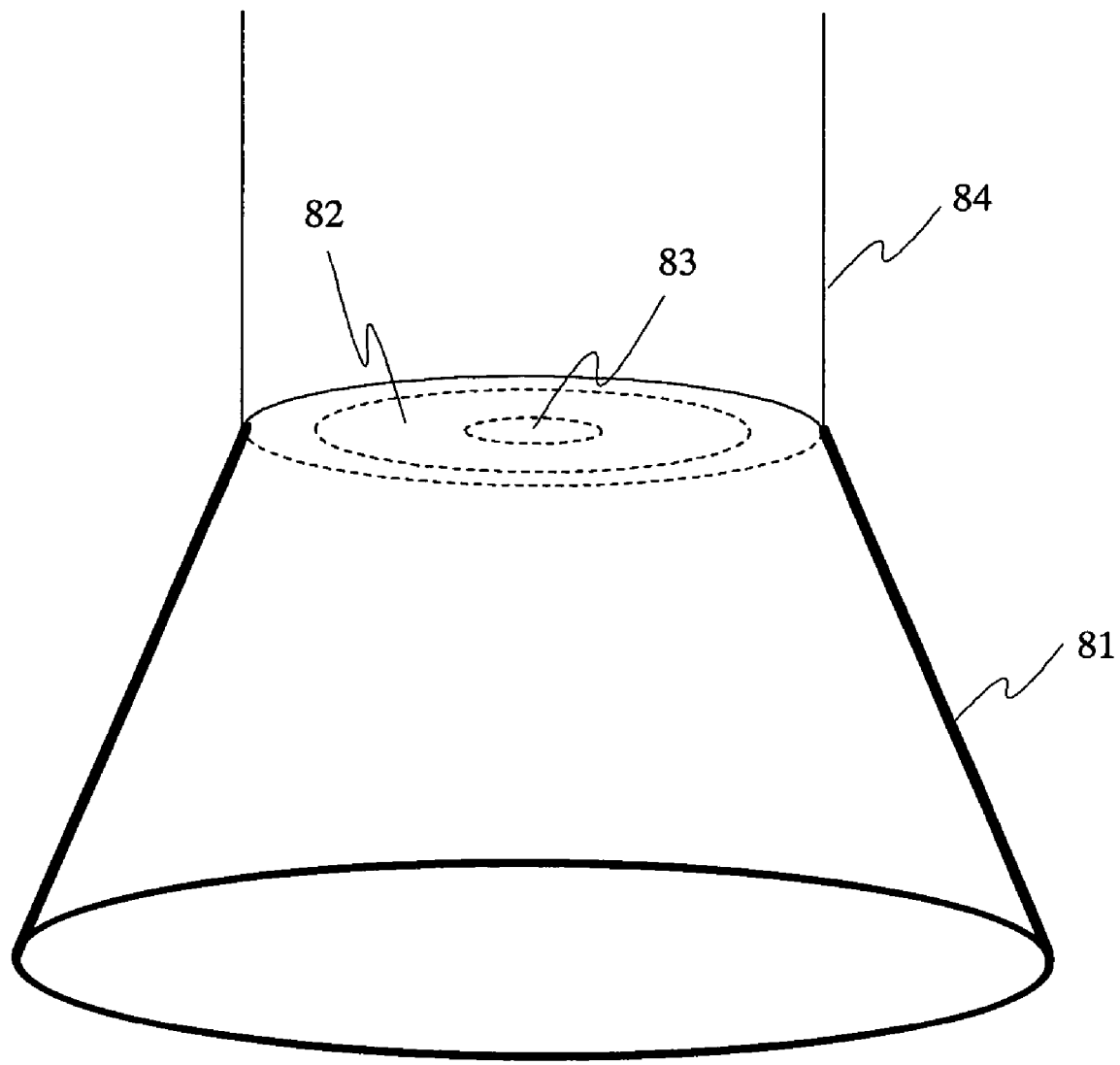
FIG. 14 is a diagram showing a body surface image pickup device according to a fourth embodiment of the present invention.

As shown in FIG. 14, according to this embodiment, instead of the electronic endoscope 2, a body surface imaging apparatus 84 is provided. The body surface imaging apparatus 84 has at its distal end portion a hood 81 to be touched to the skin, and at a distal end surface of the distal portion a plane of light injection on a light guide 82 disposed in a ring shape and a plane of incidence on an image pickup portion 83 including an objective optical system and a CCD. The hood 81 is made contact with the skin, and field sequential light beams in narrow band having spectral characteristics C1 to C3 are irradiated from the light source device 4 through the light guide 82. The image pickup portion 83 picks up an image, and the image pickup signals are transmitted to the video processor 7.

[Advantages]

According to this embodiment, the same operational advantages as that of the first embodiment can be obtained even on the body surface, and a skin cancer or the like can be detected.

Fifth Embodiment

Since a fifth embodiment is substantially the same as the first embodiment, only differences therebetween will be described. The same reference numerals are given to the same components, and the description will be omitted here.

A mucous membrane of the digestive tract such as the esophagus has a layer structure. An early cancer mainly emerges and expands within a surface layer. Therefore, in order to find a cancer at an earlier stage, a pathological change occurring within the surface layer of the mucous membrane must be captured as a picture.

However, in general, light reflected from a living body reacts with changes in layers (second and lower layers) under the surface layer (first layer) because the surface layer of the mucous membrane is significantly thin. The changes are scatterings and/or absorptions. More specifically, the changes are a pathological structure and/or the density of the blood vessel.

Therefore, an algorithm is required which is free from influences on the changes in optical characteristic of the second layer as few as possible and is used for calculating an amount of the scattering feature for emphasizing an optical characteristic (change in scattering) of the first layer.

According to the fifth embodiment, a mapping to the amount of scattering feature is obtained from a spectral image value or an observation value, which is a multiband image value.

[Structure]

Figure 15:
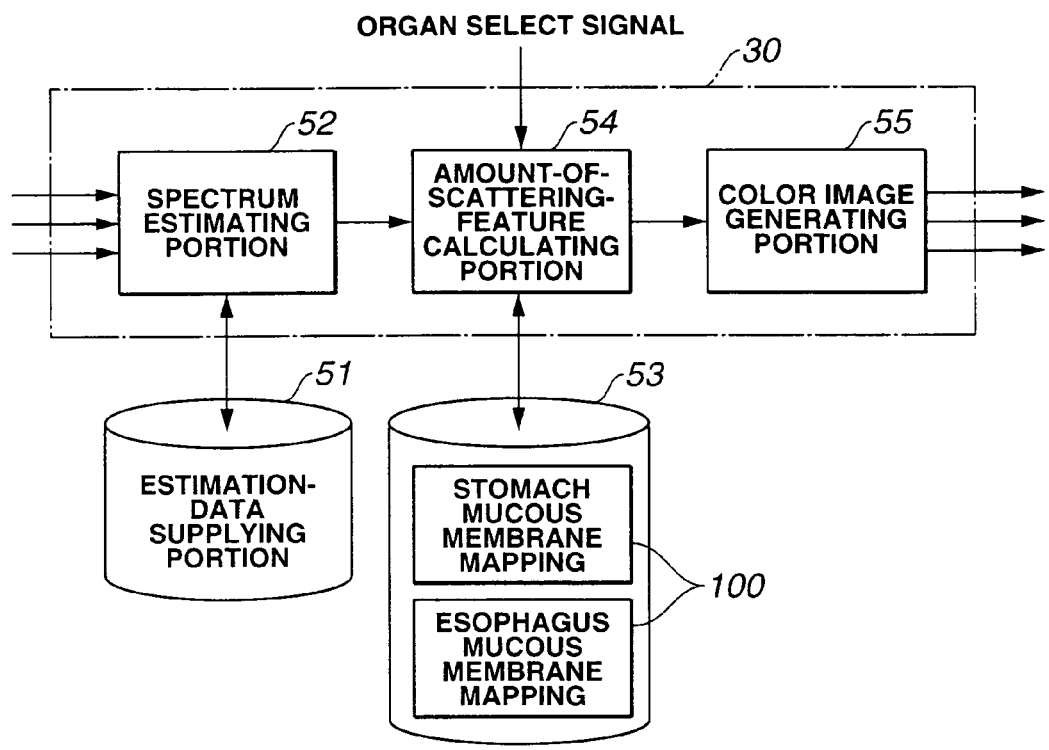
FIGS. 15 to 18 relate to a fifth embodiment of the present invention.

As shown in FIG. 15, in the image processing circuit 30, stomach mucous membrane mapping data, esophagus mucous membrane mapping data and so on as digestive tract mucous membrane mapping data 100 for each organ, which will be described later, obtained by multiple discrimination analysis are stored in the feature calculation data supplying portion 53. The scattering feature calculation portion 54 reads the corresponding digestive tract mucous membrane mapping data 100 based on an organ select signal from input means (not shown) from the feature calculation data supplying portion 53. Then, a scattering feature is calculated.

Next, the digestive tract mucous membrane mapping data 100 to be stored in the feature calculation data supplying portion 53 will be described. While the structure of the mucous membrane tissue of a digestive tract such as the esophagus is illustrated in FIG. 5, here, when the epitheliums are a first layer and the entire layers including the basal layer and lower layers are a second layer, the influence of the second layer is strongly reflected on the spectrum estimated in the spectrum estimating portion 52 of the image processing circuit 30. The change in spectrum due to the swelling of the nucleus of the first layer, for example, is masked.

According to this embodiment, a mapping to a partial space having a smaller influence of the second layer and enhancing the scattering feature of the first layer in the observation spectrum space is obtained. The obtained mapping is stored in the feature calculation data supplying portion 53 as the digestive tract mucous membrane mapping data 100.

By using the publicly known multiple discrimination analysis, such a mapping can be obtained as a linear mapping for maximizing a spectrum change depending on the characteristic change, which is the scattering feature in this case, of the first layer under a condition for minimizing a variation depending on the characteristic change of the second layer.

Figure 16:
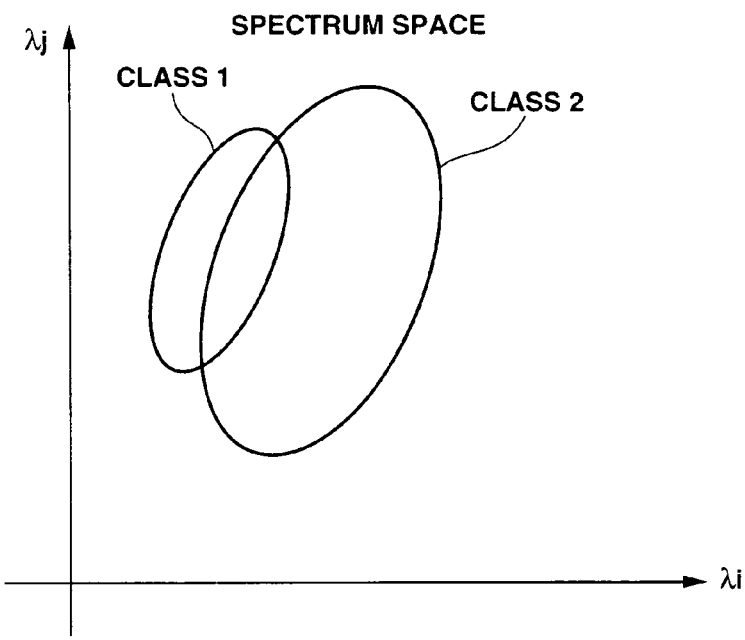

For example, it is assumed that a spectrum on the living body tissue is distributed in a spectrum space as shown in FIG. 16. Here, a class refers to a set of data having a same scattering feature of a layer, which is a target, such as the epitheliums of an early esophagus cancer. In FIG. 16, two classes are shown and refer to data sets having two kinds of epitheliums having different scattering features.

Each class includes an extension of data in accordance with changes in scattering and absorption characteristics of the layers other than the epitheliums. A mapping to the multiple discrimination space means a conversion for maximizing a distance between the classes under a condition for minimizing the extension within the classes shown in FIG. 16 (and is known as Fisher linear identification when the mapping with the two classes is linear).

Figure 17:
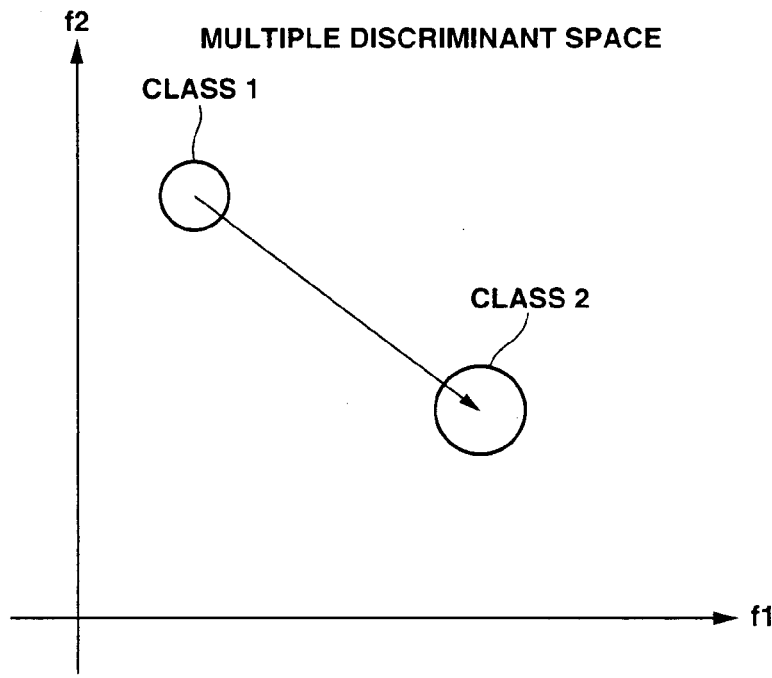

By using this mapping, the spectrum of the living body tissue in FIG. 16 is mapped to a space where a distance between the classes (inter-class distribution) is maximized as shown in FIG. 17 and a variation within each of the classes is minimized (intra-class distribution). The intra-class distribution and the inter-class distribution can be calculated by a light scattering simulation, for example.

In other words, a scattering characteristic of a living body tissue of a layer, which is a target, such as the epithelium is enhanced when the influence of the absorption/scattering characteristic of the other layers is minimized.

[Operation]

Figure 18:
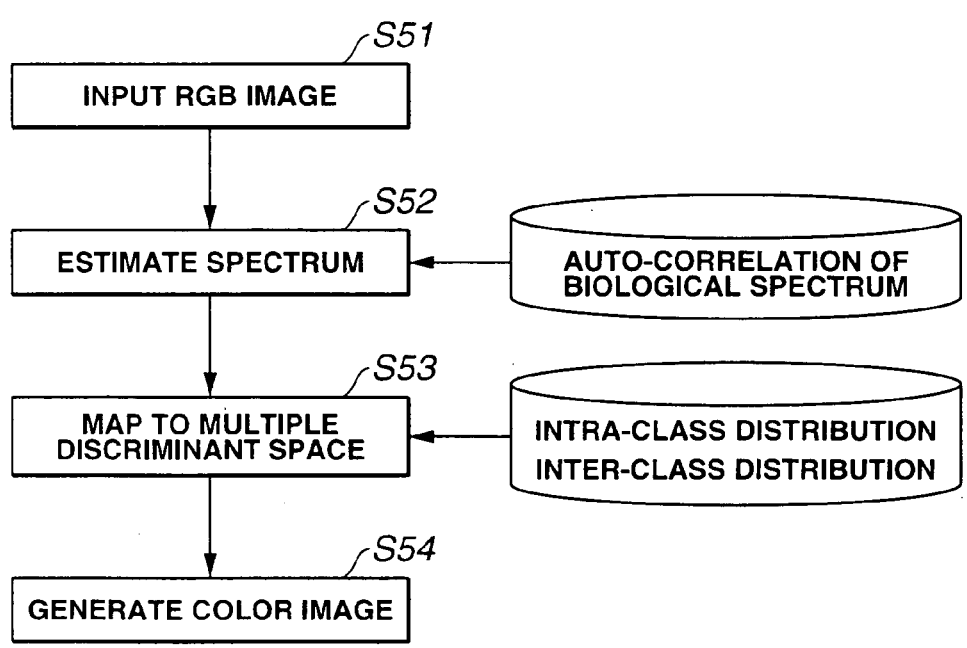

According to this embodiment, as shown in FIG. 18, when respective image data are input from the synchronized memories 27, 28 and 29 in the image processing circuit 30 at a step S51, the spectrum estimating portion 52 obtains living body spectrum auto-correlation data from the estimation data supplying portion 51 and estimates spectrums of respective pixels at a step S52. At a step S53, the scattering feature calculating portion 54 reads from the feature calculation data supplying portion 53 the digestive tract mucous membrane mapping data 100 for mapping the intra-class distribution and the inter-class distribution to an optimized space in accordance with an organ select signal, and a scattering feature is calculated. At a step S54, the color image generating portion 55 performs a display color calculation based on the scattering feature image from the scattering feature calculating portion 54. Then, in order to display the scattering feature as a color image, RGB values of the respective pixels are determined and are output to the D/A circuits 31, 32 and 33 as RGB images.

When the scattering feature space obtained by the multiple discrimination analysis is three-dimensional, the color image generating portion 55 assigns the respective axes included in the scattering feature space to RGB color channels. The maximum and minimum are previously determined for each of the axes, and the ranges of the color channels are assigned within the range.

In another color assigning method, information is assigned such that the contrast in an image can be maximum. An image is input to a computer in frame (or in field), and data is mapped to the scattering feature space within a screen. In accordance with the number of pixel values within the screen, data are distributed within the scattering feature space. The maximum distribution direction should be a direction having the direction to which the changes in scattering feature are reflected most. Therefore, by using a general method such as KL expansion, a mapping value to the maximum distribution axis is obtained. One point on the maximum distribution axis is determined as a reference point, and a color is assigned to the image in accordance with the distance therefrom. An expression having the best visual recognition is adopted like assigning a color in a hue direction.

Instead of the estimation of an object spectrum from a multiband image, a value resulting from the correction of a gain valance with respect to a multiband image value may be used. In this case, the spectrum estimating portion 52 is not required. In the gain balance correcting method, an object having a known spectral reflectance, such as a white plate, is imaged, and a gain correction is performed such that the strength ratio between the observed multiband image values can be a ratio calculated from the spectral product of the band characteristics and the known object spectral reflectance.

[Advantages]

According to this embodiment, in addition to the advantages of the first embodiment, the scattering characteristics of a living body tissue of a layer, which is a target, such as the epithelium is enhanced by minimizing the influences of the absorption/scattering characteristics of the other layers. Thus, the visual recognition characteristic is improved.

Sixth Embodiment

Since a sixth embodiment is substantially the same as the fifth embodiment, only differences therebetween will be described. The same reference numerals are given to the same components, and the description will be omitted here.

[Structure]

Figure 19:
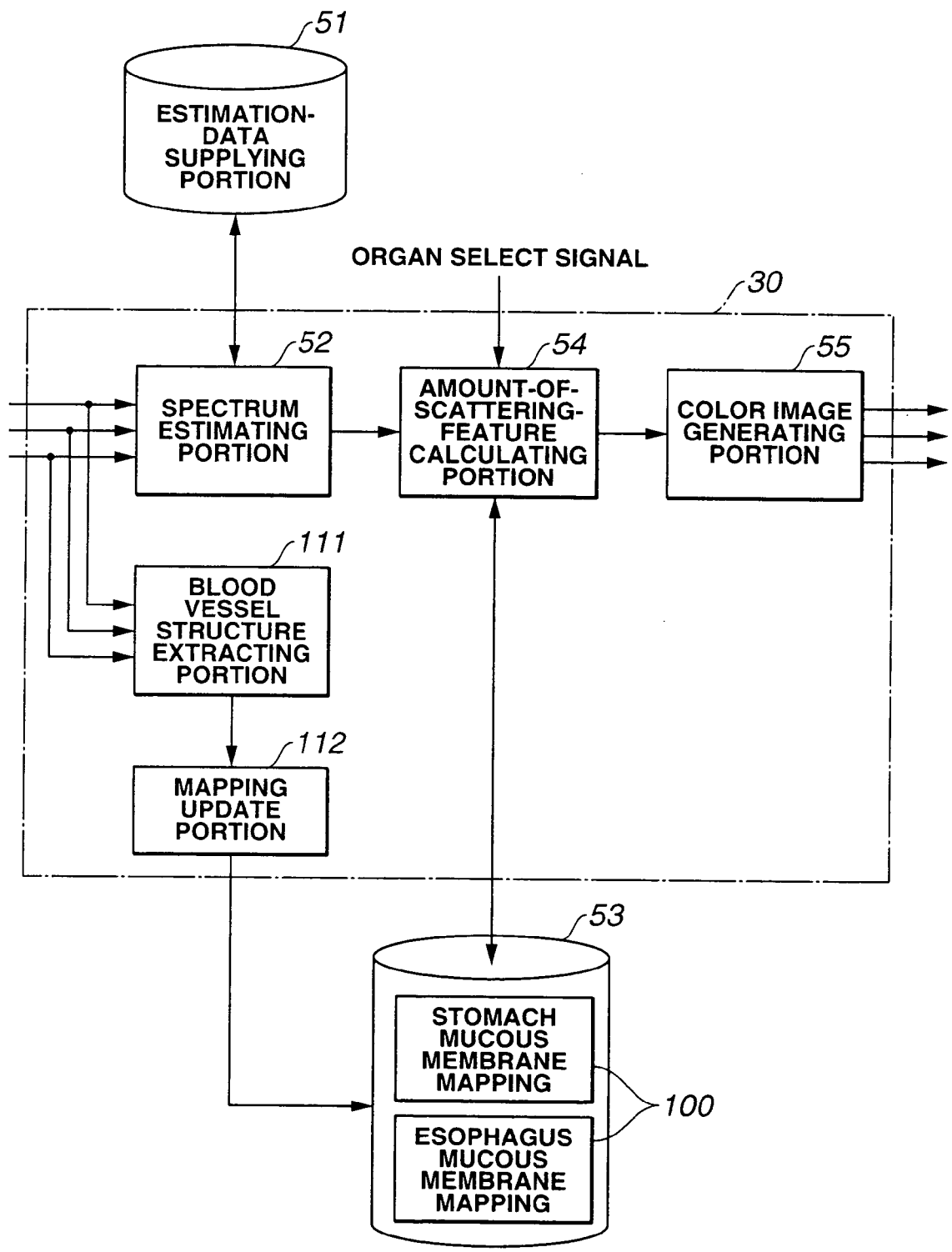

As shown in FIG. 19, the image processing circuit 30 includes a blood vessel structure extracting portion 111 and a mapping updating portion 112. The blood vessel structure extracting portion 111 extracts blood vessel structure information of a second layer (that is the entire lower layers including the basal and lower layers in FIG. 5) from image data from the synchronized memories 27, 28 and 29. The mapping updating portion 112 calculates a variation within a class (intra-class distribution) based on the blood vessel structure information extracted by the blood vessel structure extracting portion 111 and updates digestive tract mucous membrane mapping data 100 stored in the feature calculation data supplying portion 53 based on the intra-class distribution.

[Operation]

Figure 20:
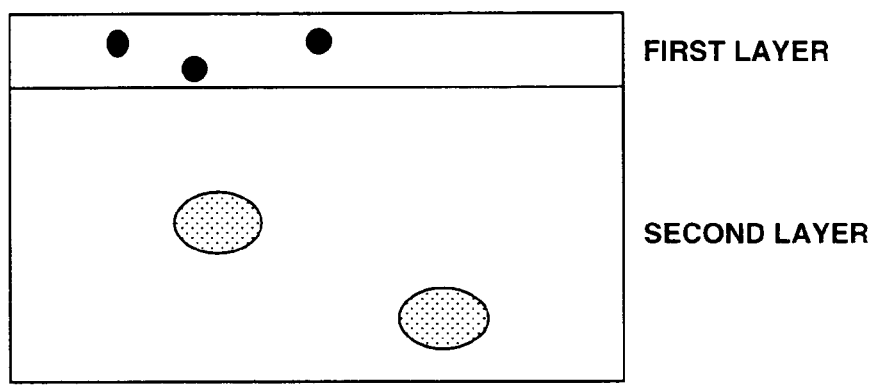
Figure 21:
Figure 22:
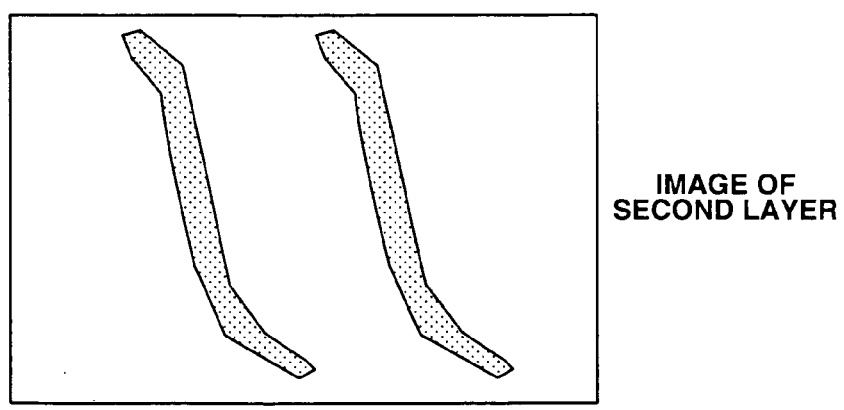

A living body tissue having a layer structure, such as an esophagus mucous membrane may have a unique blood vessel structure in which the surface layer is a capillary tube and the medium deep layer is a relatively thicker blood vessel as shown in FIG. 20. When a living body tissue having this kind of structure is observed by using bands having different center wavelengths, the blood vessel of the surface layer and the blood vessel of the medium deep layer are reproduced on the short wavelength side and on the long wavelength side, respectively, as shown in FIGS. 21 and 22 (see Japanese Unexamined Patent Application Publications No. 2002-95635, 2002-34893 and 2002-34908).

Therefore, in the data set, the characteristics of the epitheliums are the same between the position with the blood vessel and the position without the blood vessel while the other layers have different characteristics. The intra-class distribution can be estimated from the data set.

As shown in FIG. 23, at a step S71, the blood vessel structure extracting portion 111 extracts a position of the blood vessel from the RGB images by using an image (such as the B image) on the long wavelength side. A general method such as threshold processing and spatial frequency filtering processing may be applied to the extraction of the position of the blood vessel. At a step S72, the mapping updating portion 112 gathers many pixels at positions of the blood vessel and pixels excluding the blood vessel. At a step S73, the intra-class distribution is calculated, and the digestive tract mucous membrane mapping data 100 stored in the feature calculation data supplying portion 53 is updated based on the intra-class distribution.

In this case, the blood vessel structure extracting portion 111 extracts the position of the blood vessel from the RGB images by using the image (such as the B-image) on the long wavelength side from the RGB images. However, in order to obtain a band image for extracting the position of the blood vessel, an observation area may be illuminated by using a special band filter.

[Advantages]

Also according to this embodiment, the same advantages can be obtained as those of the fifth embodiment.

According to this embodiment, illumination light is separated in band on the light source side and is irradiated in order to obtain multiband images. However, the structure is not limited thereto. Multiband images may be obtained by using a band separating filter on the image picking-up side.

It is apparent that a wide variety of embodiments according to the present invention can be constructed widely based on the present invention without departing from the spirit and scope of the invention. The present invention is only limited by appended claims and is not limited by specific embodiments thereof.

INDUSTRIAL APPLICABILITY

As described above, an imaging apparatus according to the present invention is useful as an apparatus for imaging a scattering feature in an internal tissue as image information.

The invention claimed is:

1. An imaging apparatus, comprising:
    a light source device;
    an image pickup device for converting a living body observed image to video signals by using light irradiated from the light source device for observation; and
    a processor for generating a living body image from the video signals, the processor including means for generating a living body image having at least a scattering feature of a relative scattering change representing a degree of nucleus variant and structure variant of a living body tissue as image information, and
    the light source device irradiates a plurality of band light beams that exist in a band positioned as blue light in a visual light wavelength range, wherein
    the processor generates the living body image based on narrow band images obtained in synchronization with each irradiation of the plurality of band light beams and on an optical model corresponding to a particle size distribution of the living body tissue.

2. The imaging apparatus according to claim 1, wherein the image pickup device is an endoscope.

* * * * *